United States Patent [19]

Inamoto et al.

[11] 4,248,891
[45] Feb. 3, 1981

[54] 1-(1-AMINOALKYL)TRICYCLO[4,3,1,1$^{2,5}$]UN-DECANES

[75] Inventors: Yoshiaki Inamoto, Utsunomiya; Motoyoshi Osugi; Eiji Kashihara, both of Wakayama, all of Japan

[73] Assignees: Kao Soap Co., Ltd., Tokyo; Sumitomo Chemical Industries, Ltd., Osaka, both of Japan

[21] Appl. No.: 102,000

[22] Filed: Dec. 7, 1979

[30] Foreign Application Priority Data

Dec. 15, 1978 [JP] Japan .................................. 53-156178

[51] Int. Cl.$^3$ .................. A61K 31/205; A61K 31/13; C07C 87/40
[52] U.S. Cl. ................................. 424/316; 260/501.1; 424/325; 564/455
[58] Field of Search ....................... 260/563 R, 583 T; 424/316, 325

[56]  References Cited

U.S. PATENT DOCUMENTS

| | | | |
|---|---|---|---|
| 4,046,811 | 9/1977 | Bharucha et al. | 424/316 |
| 4,078,085 | 3/1978 | Inamoto et al. | 424/325 |
| 4,087,551 | 5/1978 | May | 424/325 |
| 4,101,580 | 7/1978 | Inamoto et al. | 260/563 R |

Primary Examiner—Natalie Trousof
Assistant Examiner—Vera C. Clarke
Attorney, Agent, or Firm—Blanchard, Flynn, Thiel, Boutell & Tanis

[57]  ABSTRACT

Compounds having the formula

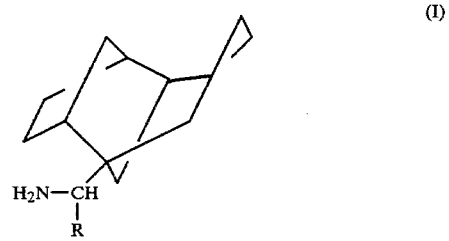

(I)

in which R is lower alkyl, and acid addition salts of said compounds. The compounds possess anti-RNA-viral activity and also an antiviral activity against herpes virus.

7 Claims, No Drawings

1-(1-AMINOALKYL)TRICYCLO[4,3,1,1$^{2,5}$]UNDECANES

The present invention relates to polycyclic amines and acid addition salts thereof. More particularly, the present invention relates to 1-(1-aminoalkyl)tricyclo[4,3,1,1$^{2,5}$]undecanes of formula (I):

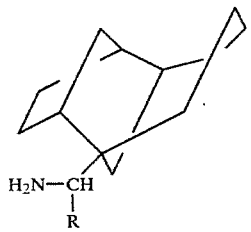

wherein R represents a lower alkyl group, and acid addition salts thereof.

It is well known that some of the so-called "cage" compounds have anti-RNA-viral activity. However, almost no compounds having anti-DNA-viral activity are known. Only Tromantadine, i.e., 1-(dimethylaminoethoxyacetamido)adamantane hydrochloride, has been reported as being an anti-DNA-viral substance (see Japanese Patent Publication No. 32526/1974). Recently, it has been reported that 1-aminotricyclo[4,3,1,1$^{2,5}$]undecane hydrochloride has an excellent effect against Newcastle disease virus, which is one of the Paramyxo viruses belonging to RNA viruses, in a chick embryo cell in vitro test system (see Japanese Patent Laid-Open No. 50150/1978 and U.S. Pat. No. 4,104,305). However, almost no other amine derivatives of tricyclo[4,3,1,1$^{2,5}$]undecane are known.

The inventors have discovered new amine derivatives of tricyclo[4,3,1,1$^{2,5}$]undecane having an antiviral activity. The present invention has been completed on the basis of this discovery.

The present invention provides 1-(1-aminoalkyl)-tricyclo[4,3,1,1$^{2,5}$]undecanes of formula (I):

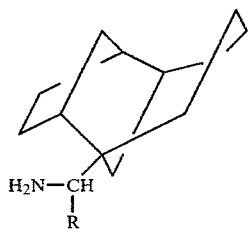

wherein R represents a lower alkyl group, and acid addition salts thereof.

Amines of the formula (I), according to the invention, are obtained, for example, by reducing the oximes of formula (II),

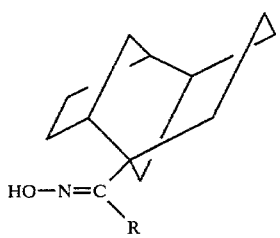

wherein R represents said lower alkyl group (hereinafter referred to as oximes (II)). The lower alkyl groups R in the above formulas, for example, are alkyl groups of 1-6 carbon atoms such as methyl, ethyl, propyl, isopropyl, butyl, amyl and hexyl. The compound wherein R is methyl is readily available and is particularly preferred.

Oximes (II) can be reduced to the amines of formula (I) by reducing the same, for example, with metallic sodium in an absolute lower alcohol (Bourveault-Blanc reaction). As the lower alcohols used, ethyl alcohol is the most suitable. In addition, as the lower alcohols, there can be mentioned propyl alcohol, butyl alcohol, t-butyl alcohol and methyl alcohol. The metallic sodium used may be in the form of either small pieces or finely divided powder particles. The lower alcohol is used generally in great excess in the reaction system because it also acts as a solvent. It is preferred to use metallic sodium in an amount several times as much as the theoretically required amount for carrying out the reduction reaction completely. Specifically, it is effective to use metallic sodium in an amount of 5 to 30 moles per mole of the oxime. The reaction proceeds at a temperature in the range of from ambient temperature up to about 100° C. When ethyl alcohol is used as the lower alcohol, it is most convenient to reflux the reaction mixture at its boiling point.

The conversion of oximes (II) into amines of formula (I) can also be effected by hydrogenation in the presence of a hydrogenation catalyst, in addition to the aforementioned method wherein it is reduced with metallic sodium in a lower alcohol. As the hydrogenation catalyst, any known hydrogenation catalysts can be used. The hydrogenation catalysts include, for example, metals such as palladium, platinum, nickel and copper as well as complexes thereof and these metals supported on activated charcoal.

The acid addition salts of amines of formula (I) can be obtained easily by neutralizing the amines of formula (I) with an acid. The acids used generally for this purpose, include both mineral acids and organic acids. As the mineral acids, there can be mentioned hydrogen halides such as hydrochloric acid, hydrobromic acid and hydroiodic acid; phosphoric acid, pyrophosphoric acid, sulfuric acid, thiosulfuric acid and boric acid. As the organic acids, there can be mentioned organic carboxylic acids including fatty monocarboxylic acids such as formic acid, acetic acid, propionic acid, butyric acid, caprylic acid and lauric acid; saturated dicarboxylic acids such as oxalic acid, malonic acid, succinic acid, glutaric acid and adipic acid; aliphatic hydroxy acids such as glyconic acid, lactic acid, malic acid, tartaric acid and citric acid; halogenated acetic acids such as monochloroacetic acid and monobromoacetic acid; and aromatic carboxylic acids such as benzoic acid, salicylic acid, p-hydroxybenzoic acid, m-hydroxybenzoic acid, phthalic acid and terephthalic acid; as well as organic sulfonic acids such as methanesulfonic acid, ethanesulfonic acid, benzenesulfonic acid and p-toluenesulfonic acid. Among these acids, hydrogen halides, particularly hydrochloric acid, are preferred because of the ease with which they can be handled.

Oximes (II) used as the starting material for preparing amines of formula (I) of the present invention can be derived from known compounds according to the following reaction scheme:

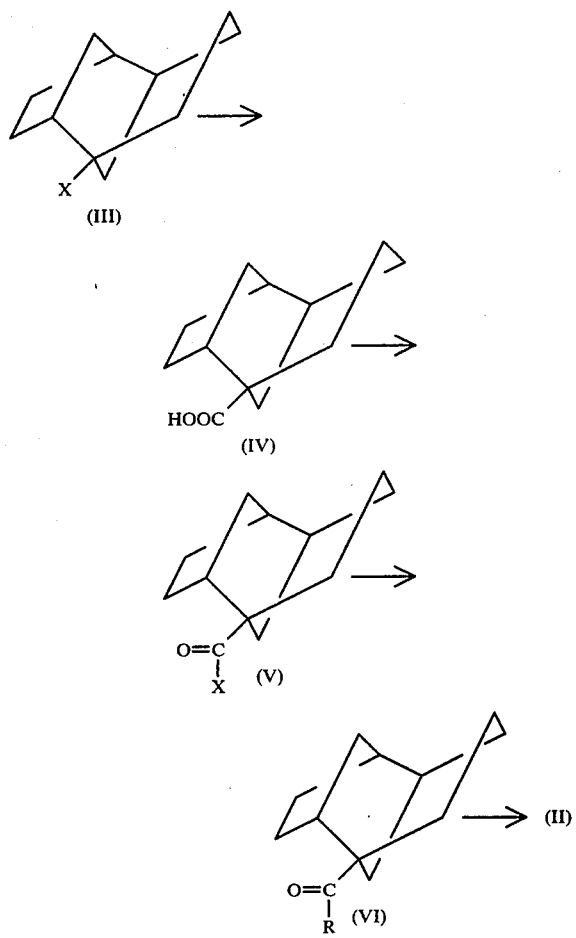

wherein X represents a halogen atom and R has the same meaning as set forth above.

1-Halogenotricyclo[4,3,1,1$^{2,5}$]undecanes of formula (III) are known compounds (see Japanese Patent Laid-Open No. 46949/1978 and U.S. Pat. No. 4,120,906). Compound of formula (III) is reacted with formic acid in the presence of sulfuric acid, to obtain carboxylic acid (IV) (see Japanese Patent Laid-Open No. 9255/1979). Carboxylic acid (IV) may be halogenated to form the corresponding acid halides in a customary manner for obtaining acid halides from carboxylic acids (see Japanese Patent Laid-Open No. 14952/1979). The carboxylic acid (IV) is preferably reacted with 1 to 10 moles, more particularly 2 to 5 moles, per mol of the carboxylic acid (IV), of thionyl halide such as thionyl chloride or thionyl bromide. The reaction can be carried out either with or without a solvent. If a solvent is used, there can be used, for example, benzene, toluene, chloroform or carbon tetrachloride. The suitable reaction temperature ranges from room temperature to the boiling point of the solvent used. A temperature close to the boiling point of the solvent is most preferred.

Ketones (VI) can be prepared by reacting the acid halides (V) with dialkylcadmiums. The dialkylcadmiums can be prepared from cadmium halides and Grignard reagents prepared from the corresponding alkyl halides. In the preparation of ketones (VI), the dialkylcadmiums are used in an amount of 1 to 2 moles per mole of the acid halides (V) and the reaction is carried out at a temperature in the range of 25° to 80° C., preferably 60° to 80° C.

Ketones (VI) can be converted into oximes (II), the starting material of the present invention, for example, by reacting the same with hydroxylamine zinc chloride salt in ethyl alcohol.

1-(1-Aminoalkyl)tricyclo[4,3,1,1$^{2,5}$]undecanes of formula (I) and acid-addition salts thereof, according to the present invention, have an anti-viral activity. Thus, they are quite useful for the treatment of virus diseases in human beings and animals. In addition, it is also found that the compounds (I) are effective as drugs for treating Parkinson's disease.

The following examples further illustrate the present invention, but the invention is not limited thereto. Processes for the preparation of starting materials are also shown in the following Preparations.

PREPARATION 1

Preparation of 1-chlorocarbonyltricyclo[4,3,1,1$^{2,5}$]undecane (formula (V): X=Cl):

Into a solution of 5.5 g (0.028 mole) of tricyclo[4,3,1,1$^{2,5}$]undecane-1-carboxylic acid (IV) in 20 ml of dry benzene was added dropwise with stirring 12 ml of thionyl chloride at room temperature. The mixture was heated under reflux for one hour. Excess thionyl chloride and benzene were distilled off and the residue was fractionally distilled. A fraction boiling at 105° to 108° C. (2 mm Hg) was collected to give 5.2 g (87% yield) of 1-chlorocarbonyltricyclo[4,3,1,1$^{2,5}$]undecane.
IR (neat):
1700 ($\nu_{C=O}$) cm$^{-1}$

PREPARATION 2

Preparation of 1-acetyltricyclo[4,3,1,1$^{2,5}$]undecane (formula (VI): R=CH$_3$):

4.0 g (28.2 mmol) of methyl iodide was added dropwise into a suspension of 0.69 g (28.2 mmoles) of metallic magnesium in 10 ml of dry diethyl ether under reflux and stirring over 30 minutes to afford methyl magnesium iodide. 4.14 g (22.56 mmoles) of cadmium chloride was added to the reaction mixture, and the ether was distilled off from the reaction mixture. Anhydrous benzene (20 ml) was added thereto and then 3.0 g (14.1 mmoles) of 1-chlorocabonyltricyclo[4,3,1,1$^{2,5}$]undecane prepared in Preparation 1 was added to the mixture. After heating at 60° to 80° C. for about 1.5 hours, water (20 ml) and then 20% H$_2$SO$_4$ (10 ml) were added thereto. The organic layer was separated and the aqueous layer was extracted with benzene. The combined organic layer and benzene extract were washed successively with water, 5% sodium carbonate and water and then dried. The solvent was distilled out to give 2.61 g (96.7% yield) of colorless, transparent, liquid 1-acetyltricyclo[4,3,1,1$^{2,5}$]undecane.

Elemental analysis: Calculated for C$_{13}$H$_{20}$O (%): C, 81.20; H, 10.48. Found (%): C, 81.5; H, 10.5.

IR (neat): 2925, 2860, 1700, 1480, 1465, 1350, 1250, 1210, 1080, 980, 900 cm$^{-1}$ $^1$H NMR (CDCL$_3$): δ 1.1~2.5 (17H) 2.0 (s, 3H, —CH$_3$)

Mass Spectrum: m/e (relative intensity): 193 (4), 192 (27, M$^+$), 149 (100), 93 (18), 83 (16), 81 (29), 79 (14), 67 (45)

PREPARATION 3

Preparation of 1-acetyltricyclo[4,3,1,1$^{2,5}$]undecane oxime (II, R=CH$_3$):

1.66 g (8.2 mmoles) of hydroxylamine zinc chloride salt was added to a solution of 2.63 g (13.7 mmoles) of 1-acetyltricyclo[4,3,1,1$^{2,5}$]undecane in ethanol (30 ml) and the mixture was heated under reflux with stirring for 3 hours. The solution was concentrated under reduced pressure, and the residue washed with water and dried to give 2.32 g (82% yield; recrystallized from diethyl ether) of 1-acetyltricyclo[4,3,1,1$^{2,5}$]undecane oxime having a melting point 157°–158° C.

Elemental analysis: Calculated for C$_{13}$H$_{21}$ON (%): C, 75.31; H, 10.21; N, 6.76. Found (%): C, 76.0; H, 10.3; N, 6.7.

IR (Nujol): 3500~3000, 2900, 1700, 1650, 1460, 1370, 1360, 1260, 1215, 1200, 1070, 1000, 990, 940, 900, 750, 720 cm$^{-1}$ $^1$H NMR (CDCl$_3$) δ: 1.3~2.5 (17H) 1.83 (s, 3H, —CH$_3$)

Mass Spectrum: m/e (relative intensity): 208 (17), 207 (100, M$^+$), 191 (19), 190 (69), 174 (19), 164 (31), 150 (51), 149 (61), 138 (71), 122 (91), 107 (38)

EXAMPLE 1

1-(1-Aminoethyl)tricyclo[4,3,1,1$^{2,5}$]undecane (I, R=CH$_3$) and hydrochloride salt thereof:

1.93 g (83.9 mmoles) of metallic sodium powder were added in small portions into a solution of 1.00 g (4.83 mmoles) of 1-acetyltricyclo[4,3,1,1$^{2,5}$]undecane oxime in anhydrous ethanol (16 ml) kept under reflux with stirring over a period of 15 minutes. Then, the reaction mixture was heated under reflux for an additional 15 minutes and the mixture was allowed to cool. The reaction mixture was diluted with water (5 ml), then neutralized with 5% hydrochloric acid and then concentrated. The residue was made alkaline with 5% aqueous sodium hydroxide solution and then extracted with diethyl ether. The ether solution was dried and concentrated to afford 0.58 g (yield 62%) of 1-(1-aminoethyl)-tricyclo[4,3,1,1$^{2,5}$]undecane.

$^1$H NMR (CDCl$_3$): δ 0.83~2.8 (m)

Mass Spectrum: m/e (relative intensity): 193 (1, M$^+$), 164 (6), 96 (31), 93 (16), 91 (16), 81 (24), 79 (28), 67 (47), 44 (100)

The amine thus obtained was dissolved in 10 ml of dry diethyl ether. Dry hydrogen chloride gas was introduced into the solution. The resulting precipitates were filtered, dried, and then recrystallized from acetone-methanol (1:1) to give 1-(1-aminoethyl)tricyclo[4,3,1,1$^{2,5}$]undecane hydrochloride.

Melting Point: 275°~276° C.

IR (Nujol): 3200~2500, 1610, 1520, 1080, 980 cm$^{-1}$

Elemental analysis: Calculated for C$_{13}$H$_{24}$HCl: C, 67.95; H, 10.53; N, 6.09; Cl, 15.43. Found: C, 66.9; H, 10.0; N, 5.9; Cl, 14.8.

Effect of the compounds (I) 1-(1-aminoethyl) tricyclo [4,3,1,1$^{2,5}$] undecane hydrochloride on experimental Influenza virus infection.

The antiviral activities were determined by the modified Horsfall's method [Tani et al., Fukuoka Igaku Zasshi, 58, 9 (1967)].

DRUG PREPARATION

The compound (I) was dissolved in sterile physiological saline for injection.

ANIMALS

ICR male mice weighing about 12 g were used in this study. Nine animals were used at each Experiment.

VIRUS

Influenza AoPR/8 was used.

DRUG EVALUATION

Five LD$_{50}$ of influenza AoPR/8 was used for infecting mice by the aerosol. Subcutaneous drug treatment started at 2 hours pre, 2, 6, 18, 30, 42, 54, 66, 78, 90, 102, 114, 126, 138 and 150 hours past the infection in order to determine the efficacy of the compound (I). Results were as follows;

|  |  | Average change in the body temperature | | |  |
|---|---|---|---|---|---|
|  | Dosage | days after the infection | | |  |
| Compound | (mg/kg) | 3 | 4 | 5 | 6 |
| 1-(1-Aminoethyl)tricyclo [4,3,1,1$^{2,5}$]undecane hydrochloride (I) | 15 | 35.6° C. | 35.7° C. | 33.9° C. | 31.2° C. |
| Control | — | 35.1° C. | 35.2° C. | 32.9° C. | 29.4° C. |

It is noted that the compound (I) has a significant difference by p<0.05, from the control with the t-examination. Furthermore, the mice which were infected with influenza changed in their body temperature and were almost dead when the body temperature decreased at lower than 30° C. It is understood that the decrease of the body temperature was tightly connected with the advance of influenza and therefore it is considered that the decrease is an important parameter on the efficacy of the drug.

The embodiments of the invention in which an exclusive property or privilege is claimed are defined as follows:

1. A compound having the formula:

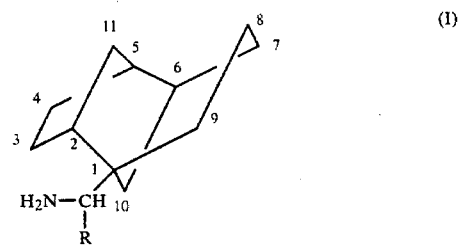

wherein R is lower alkyl, and acid addition salts thereof.

2. A compound according to claim 1 wherein R is methyl.

3. Organic acid addition salts of the compound according to claim 1.

4. Mineral acid addition salts of the compound according to claim 1.

5. Hydrogen halide acid addition salts of the compound according to claim 1.

6. A pharmaceutical anti-viral composition which comprises as an active ingredient a pharmaceutically effective amount of at least one of compounds according to claim 1 and at least one pharmaceutical inert carrier or diluent.

7. A compound according to claim 1 wherein R contains from 1 to 6 carbon atoms.

* * * * *